(12) United States Patent
Nishiuma et al.

(10) Patent No.: US 7,691,648 B2
(45) Date of Patent: Apr. 6, 2010

(54) TARGET SUBSTANCE DETECTING ELEMENT, TARGET SUBSTANCE DETECTION APPARATUS AND TARGET SUBSTANCE DETECTION METHOD

(75) Inventors: Satoru Nishiuma, Kawasaki (JP); Norihiko Utsunomiya, Tokyo (JP); Takashi Ikeda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 157 days.

(21) Appl. No.: 12/123,167

(22) Filed: May 19, 2008

(65) Prior Publication Data
US 2008/0225292 A1 Sep. 18, 2008

Related U.S. Application Data

(62) Division of application No. 11/165,504, filed on Jun. 24, 2005, now Pat. No. 7,387,901.

(30) Foreign Application Priority Data
Jun. 25, 2004 (JP) ............................ 2004-188881

(51) Int. Cl.
*G01N 33/553* (2006.01)
(52) U.S. Cl. ............. 436/526; 422/82.11; 435/288.7; 435/808; 436/524; 436/525

(58) Field of Classification Search ............... None
See application file for complete search history.

(56) References Cited

U.S. PATENT DOCUMENTS

| 2003/0012693 A1 | 1/2003 | Otillar et al. |
| 2006/0011552 A1 | 1/2006 | Utsunomiya |
| 2006/0170918 A1 | 8/2006 | Nishiuma |

FOREIGN PATENT DOCUMENTS

| JP | 3452837 | 7/2003 |
| JP | 2004093558 | 3/2004 |

OTHER PUBLICATIONS

Lyon et al., "Synthesis of Fe Oxide Core/Au Shell Nanopadicles by Iterative Hydroxylamine Seeding," Nano Letters, vol. 4, No. 4, pp. 719-723 (2004).

*Primary Examiner*—Christopher L Chin
(74) *Attorney, Agent, or Firm*—Fitzpatrick, Cella, Harper & Scinto

(57) ABSTRACT

Magnetic particles with a metal coat holding target substance captors are made to react with a target substance contained in a specimen in a solution where the magnetic particles are dispersed in a liquid medium. Subsequently, the dispersion of the magnetic particles is applied to a surface having a periodic structure that is adapted to generate plasmon resonance and a change in the plasmon resonance attributable to the concentration of the target substance held on the magnetic particles fixed magnetically to the surface is optically detected to determine the concentration of the target substance in the specimen.

10 Claims, 7 Drawing Sheets

TARGET SUBSTANCE DETECTING ELEMENT, TARGET SUBSTANCE DETECTION APPARATUS AND TARGET SUBSTANCE DETECTION METHOD

BACKGROUND OF THE INVENTION

1. Field of the Invention

This invention relates to a target substance detecting element, a target substance detection apparatus and a target substance detection method adapted to cause a target substance, e.g. proteins and DNAs, in a specimen to react highly efficiently with captors fixed to a piece of metal to improve the sensitivity of detection of the target substance.

2. Related Background Art

A number of markers (marker genes) of specific diseases such as cancer, hepatitis, diabetes mellitus, osteoporosis and so on exist in blood. The concentration of a specific protein increases in a subject when the subject contracts any of such diseases from the level observed in the healthy body of the subject. Therefore, it is possible to detect any of such serious diseases in earlier stages of contraction by monitoring the related proteins. Thus, techniques for monitoring proteins are expected to be used effectively in the next generation. One of the known techniques for analyzing unprocessed and unrefined proteins is based on a sensor for identifying a specific chemical compound by utilizing the biological ligand-analyte interaction.

Several types of sensors are known to date. Known sensors include those that utilize fluorescent immunoassay, those that utilize magnetic immunoassay and those that utilize plasmon resonance. However, all of them have a common step of fixing a ligand to the surface of the sensor and causing it to be selectively bonded to the analyte in an object of detection in a highly selective and sensitive manner in order to eliminate impurities and highly efficiently fix the desired proteins to the surface of a substrate. In the case of fluorescent immunoassay, a second ligand that is marked by a fluorescent dye is bonded to a ligand-analyte complex and the fluorescent dye is energized to observe the quantity of fluorescence and hence the concentration of analyte. In the case of magnetic immunoassay, a second ligand that is marked by a magnetic bead is bonded to a ligand-analyte complex to observe the change in the magnetic field and hence the concentration of analyte. In the case of plasmon resonance, the concentration of analyte is observed on a ligand-analyte complex formed on a metal thin film or a metal fine particle by utilizing the fact that a metal plasmon highly sensitively reacts to the change in the refractive index of the surface substance.

Japanese Patent No. 3452837 discloses a plasmon resonance sensor adapted to fix Au fine particles to the surface of a glass substrate and detect the change in the refractive index of a solvent or the extent of antigen adsorption in an antigen-antibody reaction. A sensor according to the cited invention can be arranged in a narrow place and advantageously be used for a specimen of any form.

Japanese Patent Application Laid-Open No. 2004-93558 discloses an apparatus for highly efficiently detecting the process where an object of measurement and a specific substance are bonded to and dissociated from each other by combining diffraction grating type SPR (surface plasmon resonance) with a micro channel chip to minimize the quantity of introduction of a specimen and washing liquid.

There is a document disclosing a method of preparing core-shell type fine particles by coating ferrite with gold and observing optical characteristics (absorption spectrum) thereof (NANO LETTERS, 2004, vol. 4, No. 4, p 719-723).

With the technique disclosed in Japanese Patent Application Laid-Open No. 2004-93558, diffusion-controlling due to the appearance of concentration gradient of the target substance is suppressed by injecting a specimen into a very small flow path and transferring it by liquid in order to cause the target substance to highly efficiently react with captors. Then, the concentration of the target substance captured by the fixed captors is detected by detecting the change in the plasmon resonance. In other words, the cited invention requires a special structure for suppressing diffusion-controlling due to the appearance of concentration gradient of the target substance when the specimen is brought to contact with the surface where plasmon resonance is generated. In other words, the conventional art needs improvements.

SUMMARY OF THE INVENTION

In view of the above-identified circumstances, it is therefore an object of the present invention to provide a combination of a detecting element and magnetic particles that can realize high sensitivity measurements by causing a target substance dispersed in a liquid medium to react with captors so as to suppress diffusion-controlling and, subsequently to the reaction, fixing in a simple and easily treatable manner the target substance captured by the captors to the surface of the detecting element that is provided with a periodic structure adapted to generate plasmon resonance. Another object of the present invention is to provide a detection apparatus and a detection method adapted to use at least a detection means capable of optically detecting the plasmon resonance in the specimen to be measured that is obtained by using a combination of the detecting element and magnetic particles.

In an aspect of the present invention, there is provided a target substance detecting element for detecting a target substance in a specimen by utilizing plasmon resonance, said detecting element comprising:

a base member having a surface adapted to magnetically fix magnetic particles with a metal coat holding captors having a bonding ability relative to said target substance, the surface having a periodic structure adapted to generate plasmon resonance;

said detecting element being adapted to detect plasmon resonance by allowing exciting light to strike the surface at the time of fixing said magnetic particles to the surface of said base member having said periodic structure and determine the quantity of bonding of the target substance to the magnetic particles from a detected change in the plasmon resonance due to the bonding of said target substance to the magnetic particles.

In another aspect of the present invention, there is provided a target substance detection apparatus for detecting a target substance in a specimen, said apparatus comprising:

bonding means for bonding said target substance and magnetic particles with a metal coat holding captors having a bonding ability relative to said target substance;

fixing means for magnetically fixing said magnetic particles to a detecting element comprising a base member having a surface with a periodic structure adapted to generate plasmon resonance;

light source means for entering exciting light into said periodic structure;

detection means for optically detecting the plasmon resonance generated by entering exciting light into said periodic structure; and quantification means for determining the quantity of bonding of said target substance to the magnetic particles on the basis of a change in the plasmon resonance due to the bonding, if any, of said target substance to the magnetic particles as detected by said detection means.

In still another aspect of the present invention, there is provided a target substance detection method for detecting a target substance in a specimen, said method comprising:

a bonding step of bonding said target substance and magnetic particles with a metal coat holding captors having a bonding ability relative to said target substance;

a fixing step of magnetically fixing said magnetic particles to a detecting element comprising a base member having a surface with a periodic structure adapted to generate plasmon resonance; and a quantification step of detecting the plasmon resonance generated by entering exciting light into the periodic structure having said magnetic particles fixed thereto and determining the quantity of bonding of said target substance to the magnetic particles on the basis of a detected change in the plasmon resonance due to the bonding of said target substance to the magnetic particles.

Thus, according to the present invention, it is possible to suppress diffusion-controlling and improve the reaction efficiency of a target substance by means of a simple technique of causing the target substance to react with magnetic particles having captors on the surface and coated with metal (metal coated fine particles). Additionally, according to the invention, it is possible to detect a target substance in a specimen by fixing the magnetic particles that have sufficiently reacted with the target substance to a substrate, utilizing magnetic force and also plasmon resonance that can be highly sensitively detected by a detector.

DETAILED DESCRIPTION OF THE PREFERRED EMBODIMENTS

A detecting element for detecting a target substance in a specimen, utilizing plasmon resonance, according to the invention is designed to be utilized with a detection method of using magnetic particles holding captors having an ability of bonding itself to the target substance on the surface of the metal coat layer thereof as detection agent. The detecting element has a base member showing a surface adapted to magnetically fix such magnetic particles and bearing a periodic structure adapted to generate plasmon resonance.

It is possible to prepare a kit for detecting a target substance that is adapted to detect the plasmon resonance generated by causing exciting light to strike the surface when the magnetic particles are fixed to the surface of the base member having the periodic structure and determine the quantity of bonding of the target substance to the magnetic particles on the basis of the change in the detected plasmon resonance due to the bonding of the target substance to the surface of the magnetic particles at least by means of a detecting element according to the invention and magnetic particles having captors on the surfaces thereof that is able to bond itself to a target substance. Further, it is possible for the kit to comprise a detection means for detecting plasmon resonance generated by causing exciting light to strike the surface of the base member when the magnetic particles are fixed on the surface having the periodic structure of the detecting element (as needed, comprise an analyzing means such as a computer for analyzing detected data, and the like).

Now, the present invention will be described by referring to the accompanying drawings that illustrate preferred embodiments of the invention. While the present invention will be described in detail by way of specific embodiments, the present invention is by no means limited to them.

Firstly, the first embodiment of the invention will be described by referring to the related drawings.

(1-1. Agent for Detecting Target Substance)

Figure 2:
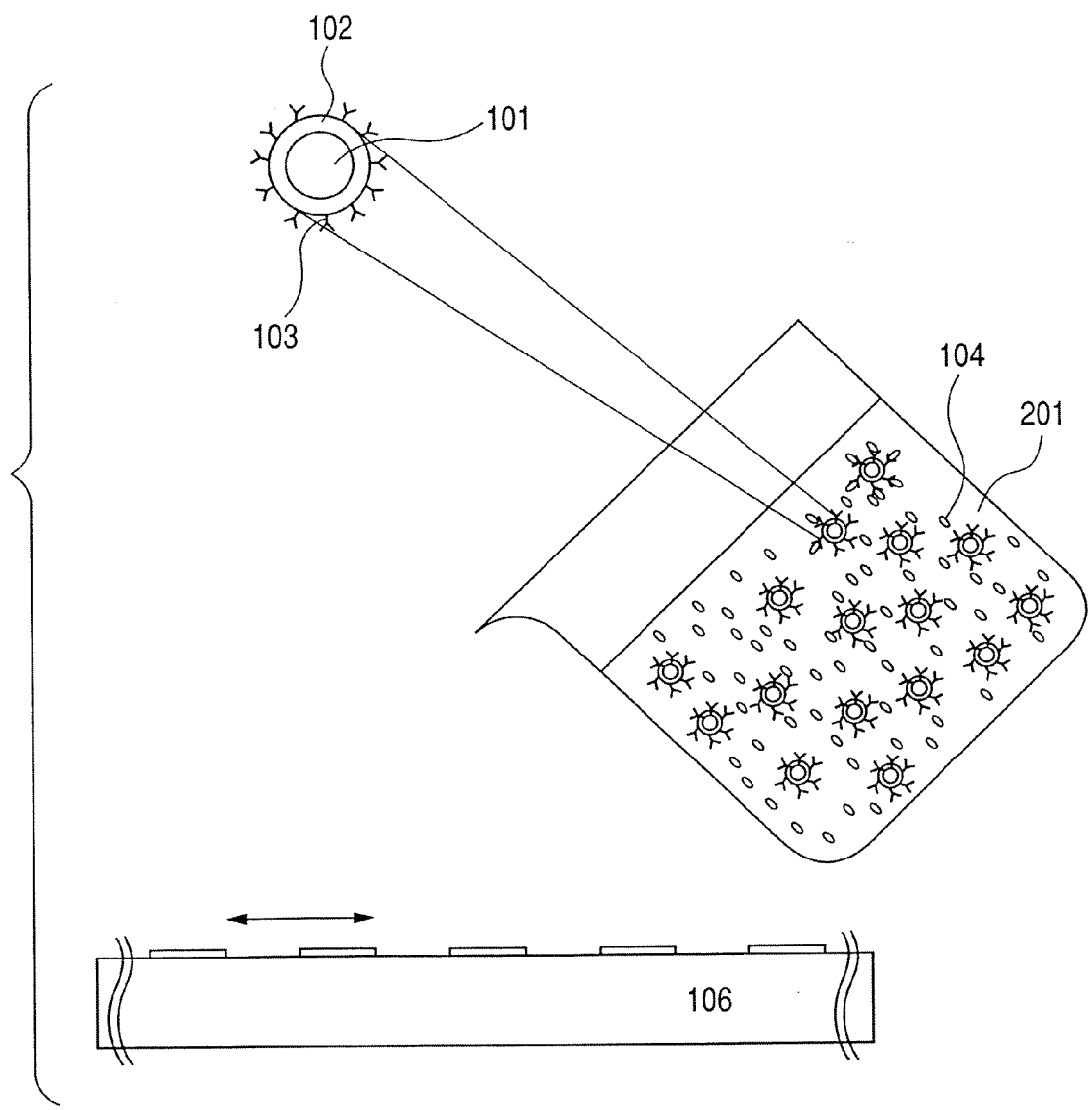
FIG. 2 is another schematic illustration of the first embodiment of the present invention.

Firstly, the structure of magnetic particles that operate as agent for detecting a target substance will be described by referring to FIG. 2. FIG. 2 shows a stage where target substance 104 is added to liquid containing magnetic particles, causing target substance captors 103 fixed onto the metal layers 102 of part of the magnetic particles to capture the target substance and applying the magnetic particles to a detecting element base member 106. The target substance detecting magnetic particles show a core-shell structure where a core 101 of a magnetic material is covered by a metal layer 102. Additionally, target substance captors 103 are fixed onto the metal layer 102 that forms the surface of the magnetic particle. While the magnetic material of the core 101 is selected from metal substances including iron, cobalt and nickel as well as oxides, alloys and complexes of such metals, the use of a ferromagnetic material is preferable for the purpose of the present invention and the use of a superparamagnetic material is more preferable for the purpose of the present invention. Generally, a ferromagnetic material does not show any hysteresis and shows superparamagnetism that is free from residual magnetization when the particle diameter of the ferromagnetic material is not greater than hundreds to tens of several nanometers although it shows saturation in a low magnetic field. Therefore, it is desirable that the core 101 shows a size that allows superparamagnetism to appear.

Any metal can be used as material for the metal layer 102 so long as it is suited for detecting plasmon resonance. In other words, any metal element can be used for the metal layer 102 so long as it can generate plasmon resonance, although examples of metals that can preferably be used for the metal layer 102 include those having a complex dielectric constant $\in$ defined by $|\in1|>>\in2$, $\in1<0$ when $\in=\in1+i\in2$ such as gold, silver, copper, aluminum, zinc and potassium.

While there are no limitations to the film thickness of the metal layer 102 so long as the fine particles can be caught and held by means of the internal magnetism by way of the metal layer 102, it is preferable that the size (diameter) of the fine particles including the metal layer 102 is within a range between 4 nm and 300 nm. While a single particle of a magnetic material operates as core in FIG. 2, the core may be alternatively be formed by dispersing a plurality of magnetic particles that show superparamagnetism by the size thereof in a non-magnetic material such as resin.

The target substance captors 103 fixed to the surface of the metal layer 102 are not subjected to any particular limitations so long as they form an specifically bonded couple with the target substance. The means for bonding the target substance and the captors may be chemical bonding. More specifically, the captors may be an antibody or a nucleic acid. Thus, an agent solution containing captor fine particles for capturing the target substance as agent in a solution is prepared in the above-described manner.

While the solution for dispersing magnetic particles having captors is not subjected to any particular limitations, it is preferable that it can stably disperse magnetic particles without producing coagulations and shows a pH value that allows antigen-antibody reactions and DNA hybridization reactions to take place.

More specifically, the target substance contained in the specimen may be a non-bio-substance or a bio-substance.

Examples of non-bio-substances that are of industrial value include PCBs and dioxins with different numbers/positions of chlorine substitutions that are environment pollutants and endocrine disturbing substances, or so-called environmental hormones.

Bio-substances are substances selected from nucleic acids, proteins, sugar chains, lipids and complexes thereof. More particularly, bio-substances are substances containing biomolecules selected from nucleic acids, proteins, sugar chains and lipids. Specific examples of bio-substances to which the present invention is applicable includes substances that contain any of DNA, RNA, aptamers, genes, chromosomes, cell membranes, viruses, antigens, antibodies, lectins, haptens, hormones, receptors, enzymes, peptides, sphingoglycolipids and sphingolipids. Additionally, bacteria and cells that produce such a "bio-substance" can be target substances and hence can be defined as "bio-substances" for the purpose of the present invention.

(1-2. Target Substance Detecting Element)

Figure 1A:
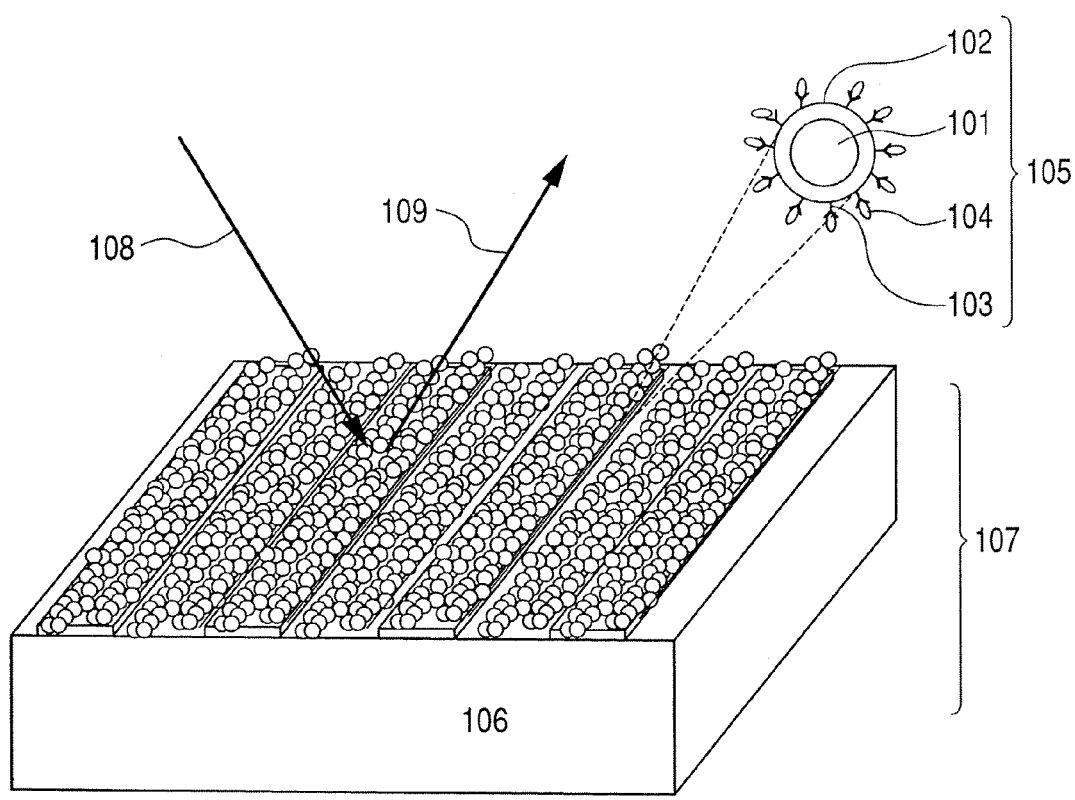
FIGS. 1A and 1B are schematic illustrations of a first embodiment of the present invention.
Figure 1B:
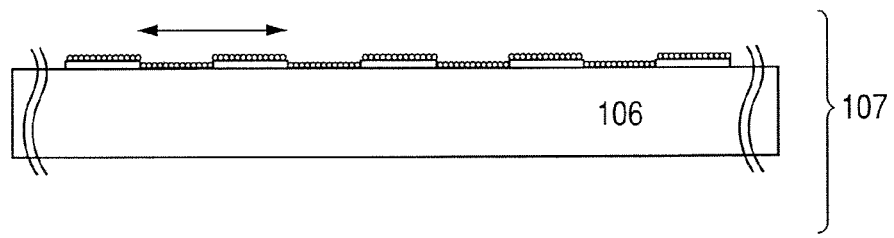

Now, a target substance detecting element according to the invention will be described by referring to FIG. 1. A target substance detecting element according to the invention comprises a base member 106 made of a magnetic material and having a surface showing a cyclic undulated structure and complexes 105 of magnetic particles that have captured a target substance are arranged on the surface by utilizing a magnetic interaction. As a mixed solution 201 containing captor fine particles that have captured the target substance and those that have not captured the target substance is dropped onto the surface showing a cyclic undulated structure of the base member 106 as illustrated in FIG. 2, a magnetic interaction takes place so as to arrange the magnetic particles on the entire surface of the base member so that the surface operates as diffraction grating that can detect plasmon resonance relative to visible light. Since the magnetic particles and the target substance react with each other in a dispersed state in the liquid medium as shown in FIG. 2, the reaction can be conducted efficiently by stirring the liquid medium, if necessary.

The base member 106 is made to have a periodic structure of a size substantially equal to the wavelength of light that is adapted to detect plasmon resonance. More specifically, the base member 106 shows a structure made of a magnetic material and having cyclically arranged undulations on the surface. Examples of magnetic materials that can be used for the base member include metals such as iron, cobalt and nickel as well as oxides, alloys and complexes of such metals. The base member may be formed by using a material showing a high magnetic permeability such as ferrite, glass or a metal oxide and applying a magnetic field thereto in order to fix magnetic particles. It is preferable that any of the above listed materials is used in an appropriate way.

It is preferable that several detecting elements are prepared as samples by using diffraction gratings to which magnetic particles that have captured the target substance and those that have not captured the target substance are fixed and subjected to various tests using an analytical technique for preventing the characteristics of the elements from being influenced by parameters other than those of the bonding of the target substance.

(1-3. Principle and Method of Detection of Target Substance)

Figure 3A:
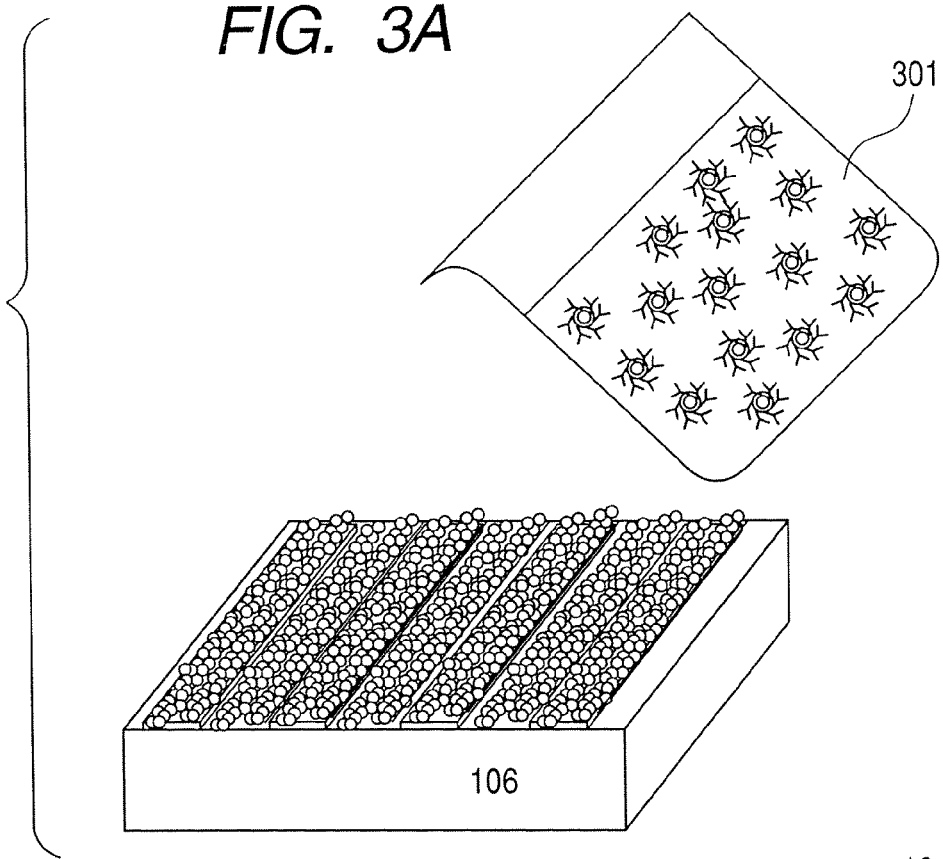
FIGS. 3A and 3B are still other schematic illustrations of the first embodiment of the present invention.
Figure 3B:
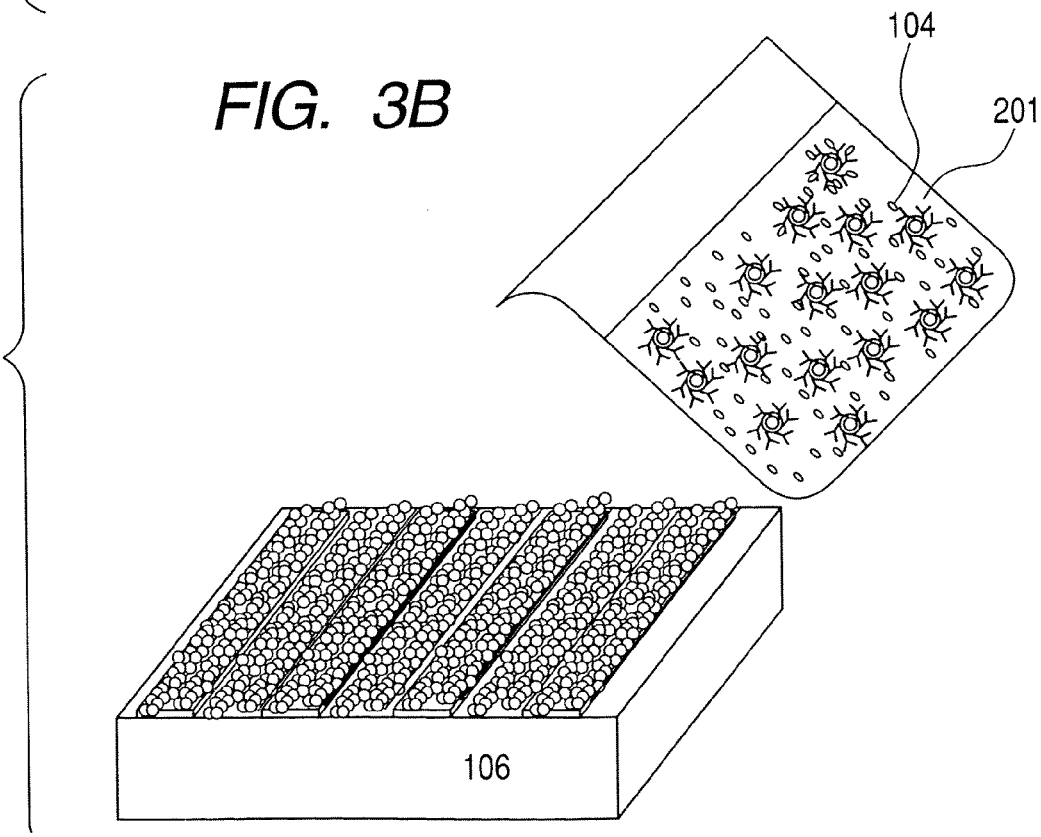
Figure 7:
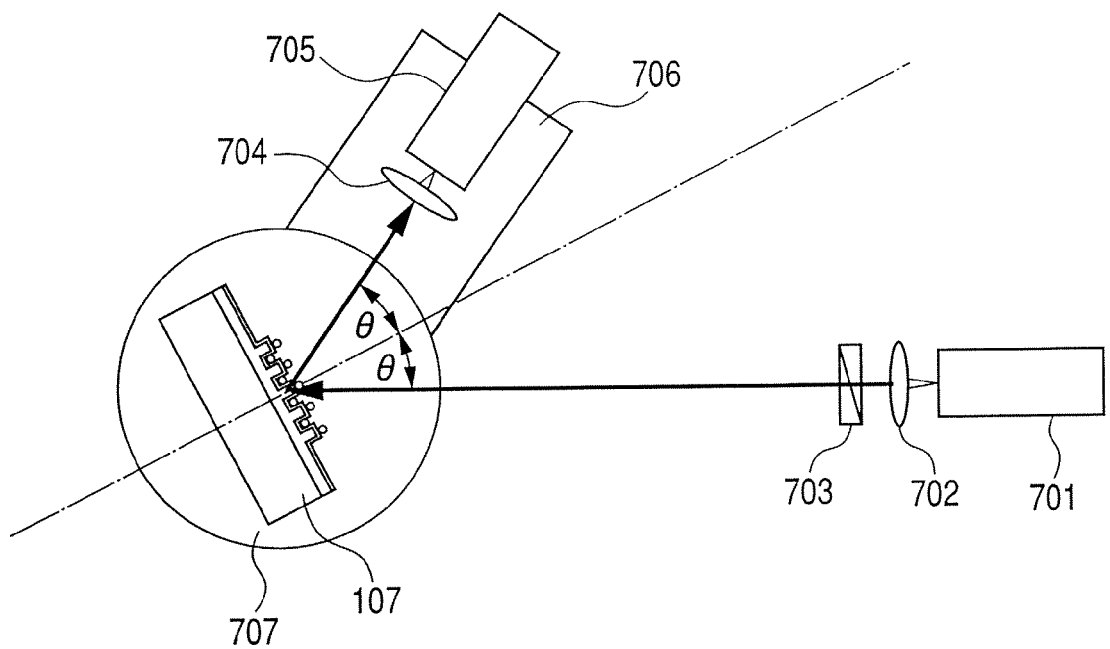
FIG. 7 is a schematic illustration of Examples 1 through 3 of the present invention.
Figure 8:
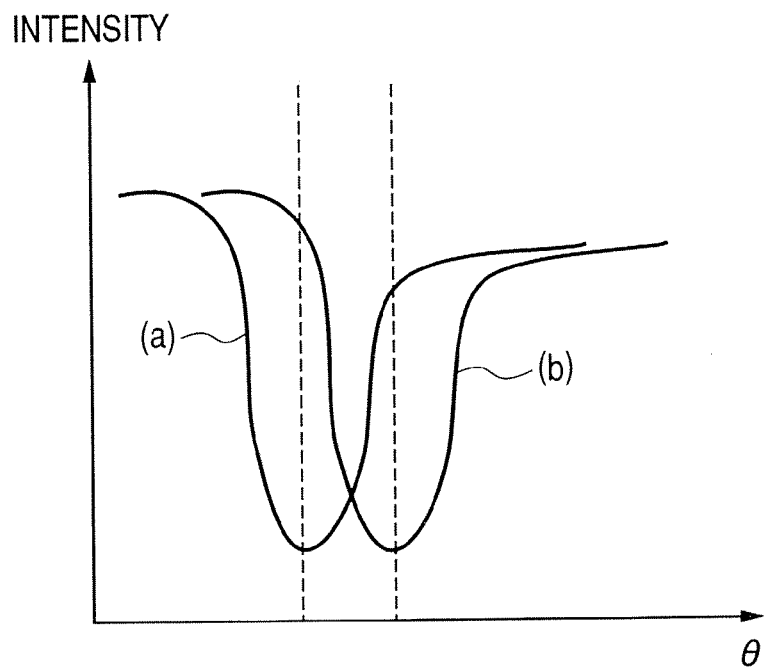
FIG. 8 is a schematic illustration of another example of the present invention.

Now, the principle and the method of detection of the target substance that utilize an element having an undulated structure will be described by referring to the related drawings. Firstly, a solution containing magnetic particles having captors in the metal coat layer of gold thereof is adjusted to a desired concentration (by preparing a solution containing magnetic particles having a metal coat and subsequently bonding captors to and around the metal layer). The solution is divided into a part for reference and a part for detecting the target substance. Then, the magnetic particle solution for detecting the target substance is made to react with the target substance as shown in FIG. 2 and subsequently, the two parts of the solution are made to react by a same quantity relative to a detecting element as shown in FIGS. 3A and 3B. As a result of the reaction, magnetic particles are fixed to the surface having a periodic structure of the base member. Then, polarized light is made to strike the detecting element for reference and the detecting element for detecting the target substance as shown in FIGS. 1 and 7. Reflected light is made to angularly scan to observe the intensity of reflected light. With this arrangement, it is possible to obtain a spectrum showing the angular dependency of the intensity of reflection as shown in FIG. 8 and hence highly sensitively observe the concentration of the target substance that has been bonded to magnetic particles. In FIG. 8, (a) indicates the outcome of observation of the detecting element for reference and (b) indicates the outcome of observation of the detecting element for detecting the target substance. Since the angle of incidence at which the intensity of reflected light is attenuated by plasmon resonance shifts depending on the concentration (quantity) of the target substance captured by the magnetic fine particles by way of the captors, it is possible to determine the concentration (captured quantity) of the target substance from the change in the angle-dependent spectrum that is based on the concentration (captured quantity) of the target substance. More specifically, the peak position of attenuation in the intensity of reflected light of the detecting element for reference relative to the angle-dependent spectrum is observed in advance by using correlation samples at various concentrations and an calibration curve (calibration data) is determined in advance. Then, it is possible to detect and quantify the target substance in the measuring specimen from the distance of the shift of the peak position of attenuation in the intensity of reflected light in the detecting element for detecting the target substance on the basis of the prepared data.

Figure 4:
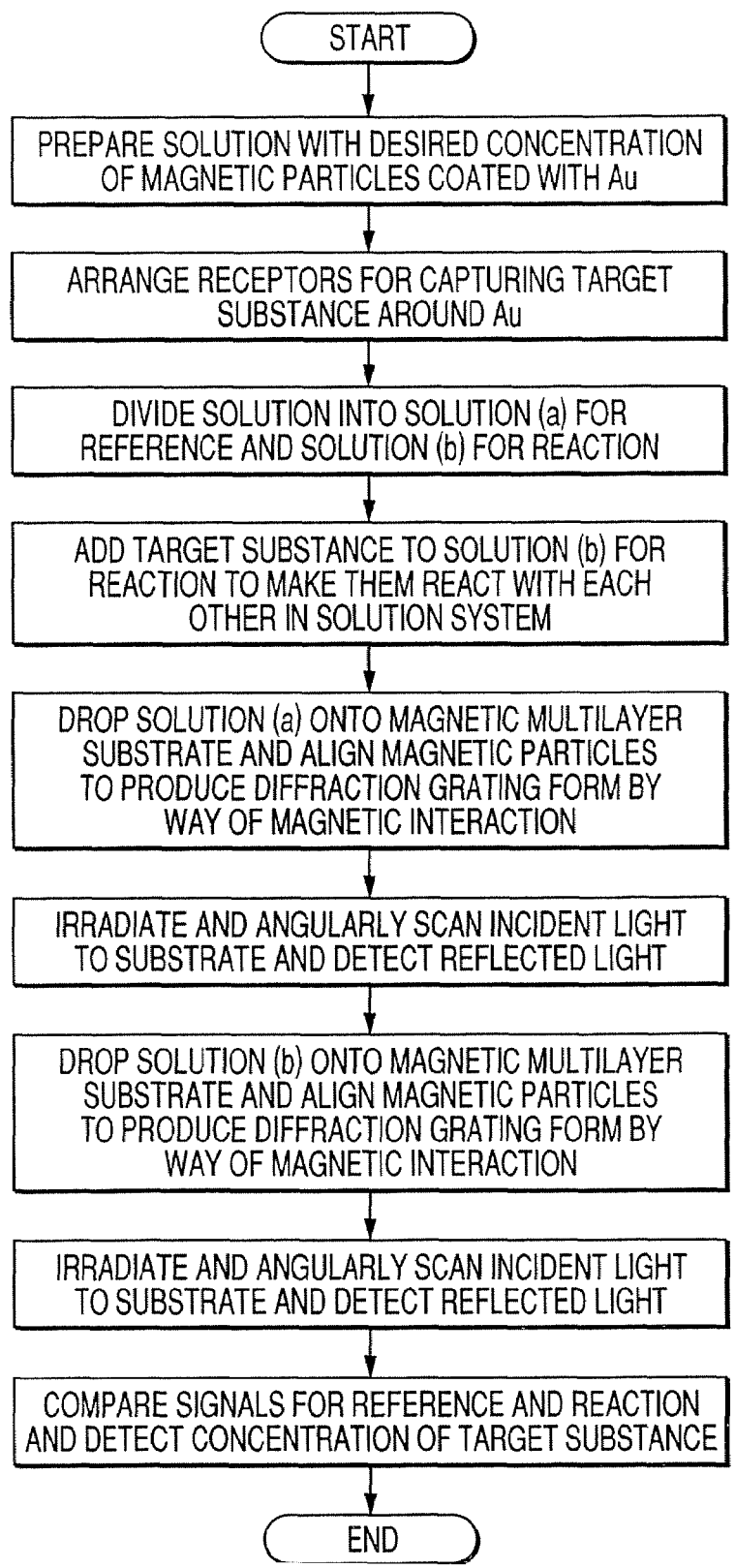
FIG. 4 is still another schematic illustration of the first embodiment of the present invention.

An angular-dependent spectrum can be observed by means of a known optical detection apparatus and it is possible to automatically analyze the obtained data by means of a computer program for utilizing an calibration curve that is prepared in advance and installed in a computer. Such automation can be applied to the second embodiment, which will be described hereinafter. FIG. 4 is a flow chart of steps from the reaction step to the detection and quantification steps.

(2-2. Target Substance Detecting Element)

Now, the second embodiment of the present invention will be described below by referring to FIGS. 5A and 5B. Magnetic particles to be used for detecting a target substance can be prepared by means of a technique similar to the one described above for the first embodiment.

The target substance detecting element will be described by referring to FIGS. 5A and 5B. FIG. 5A is a schematic perspective view and FIG. 5B is a schematic cross sectional view of the embodiment of target substance detecting element. The target substance detecting element comprises a base member 502 showing a high magnetic permeability and having a cyclic undulated structure and a magnet 501 arranged on the rear surface of the base member 502. As a mixed solution 201 containing complexes 105 that have captured the target substance and magnetic particles that have not captured the target substance is dropped on the base member 502, a magnetic interaction takes place and the magnetic particles are arranged on the entire surface of the base member so that the surface of the detecting element 503 operates as diffraction grating relative to visible light.

The magnet 501 may be an electric magnet, a permanent magnet or some other magnet that is selected appropriately. The base member 502 is made of a material showing a high magnetic permeability and has cyclic undulations on the surface thereof. Specific examples of materials that can be used for the base member include ferrite, glass and Permalloy. The target substance can be detected on the basis of the principle and by means of the technique described above by referring to the first embodiment.

(3-2. Target Substance Detecting Element)

Now, the third embodiment of the present invention will be described below by referring to FIG. 6. An agent for detecting a target substance can be prepared by means of a technique similar to the one described above by referring to the first embodiment.

The target substance detecting element will be described by referring to FIG. 6. The target substance detecting element 604 comprises a base member 601 formed by cyclically arranging a magnetic material 602 and a non-magnetic material 603. As a mixed solution 201 containing complexes 105 that have captured the target substance and magnetic particles that have not captured the target substance is dropped on the surfaces of parts of the magnetic material of the base member 106, the complexes and the magnetic particles are arranged on the entire surfaces of the parts of the magnetic materials of the base member 106 so that they operate as diffraction grating that can detect plasmon resonance relative to visible light.

The base member 601 is formed as a multilayer structure of the magnetic material and the non-magnetic material and the surface thereof is preferably mirror-polished to undulations of a fraction of the wavelength of light and coated with metal. The magnetic material 602 may be selected from metal substances including iron, cobalt and nickel as well as oxides, alloys and complexes of such metals. The magnetic material 602 is preferably selected from ferromagnetic materials and ferrimagnetic materials for this embodiment. The non-magnetic material 603 is selected appropriately from glass materials such as $SiO_2$ and $Al_2O_3$ and metal oxides.

The target substance can be detected on the basis of the principle and by means of the technique described above by referring to the first embodiment.

EXAMPLES

Now, the present invention will be described further by way of examples, although the present invention is by no means limited by the description of the examples.

Example 1

Preparation of Magnetic Particles

Magnetic particles coated with gold can be prepared by means of the method described in NANO LETTERS, 2004, Vol. 4, No. 4, pp. 719-213. Firstly, chlorides of Fe (II) and Fe (III) are put into an alkali solution to cause co-precipitation of $Fe_3O_4$ particles. Then, the $Fe_3O_4$ particles are separated and heated gradually in the atmosphere to obtain particles of $\gamma\text{-}Fe_2O_3$. Gold is formed by reducing $Au^{3+}$ on the surface of the $\gamma\text{-}Fe_2O_3$ particles. As a result of the above-described process, it is possible to produce core-shell type fine particles with a diameter of about 60 nm.

An ethanol solution of 11-mercaptoundecanoic acid having thiol-groups that shows a strong affinity for gold is added to the solution of fine particles having a core-shell structure prepared in a manner as described above in order to modify the surfaces of the fine particles. Under this condition, an aqueous solution of N-hydroxysulfosuccinimide (available from Dojindo Laboratories) and an aqueous solution of 1-ethyl-3-[3-dimethylamino]propyl]carbodiimide hydrochloride (available from Dojindo Laboratories) are added to the above solution and incubated at room temperature for 15 minutes. As a result, succinimide groups are exposed to the surfaces of the fine particles. Subsequently, an anti-human-insulin monoclonal antibody/2-[N-morpholino]ethane sulfonic acid buffer solution (pH 6.0) that is specific to the target substance is added as antibody to be fixed and further incubated at room temperature for 2 hours. Anti-human-insulin monoclonal antibody is fixed to the surfaces of the fine particles by causing the succinimide groups arranged on the metal surface and the amino groups of the anti-human-insulin monoclonal antibody to react with each other. The un-reacted succinimide groups on the surfaces of the fine particles are dissociated by adding hydroxylamine hydrochloride.

An agent solution containing captor fine particles for capturing the target substance that operate as agent in the solution can be prepared by the above-described process.

(Reaction with Target Substance)

Firstly, same quantities of the above-described agent solution are taken respectively for reference and for measurement. Insulin is added to the agent solution for measurement as target substance and made to react. The reaction can be promoted by stirring the solution by means of a stirrer.

(Preparation of Target Substance Detecting Element)

The process of preparing a target substance detecting element will be described by referring to FIGS. 3A and 3B. Diffraction grating type base bodies 106 with a cycle of 550 nm, an amplitude of 50 nm size, a surface area of 3 mm square (i.e. 3 mm×3 mm) are prepared by electron beam lithography. To do this, an agent solution for reference and an agent solution to which insulin is added and made to react are dropped respectively on a base member for reference (FIG. 3A) and a base member for measurement (FIG. 3B) to make them operate as diffraction gratings adapted to fix the target substance on the base member 106 by way of a magnetic interaction. While the diffraction grating type base bodies are prepared by electron beam lithography in the above description, they may alternatively be prepared by some other technique such as one that utilizes interference with exposure to light.

(Detection of Target Substance)

Now, the operation of detecting the target substance will be described by referring to FIG. 7. A laser diode (DL3038-033, tradename, available from Sanyo Electric Co., Ltd.) is used for light source 701 and a flat/convex lens (plano-convex lens 5 mmφ, available from Sigma Koki Co., Ltd.) is used for collimator lens 702, while a visible light polarizing filter (SPF-30C-32, tradename, available from Sigma Koki Co., Ltd.) is used for polarizing filter 703. The above listed components of incident-side optical system are rigidly secured to a surface table. A plano-convex lens (plano-convex lens 5 mmφ, available from Sigma Koki Co., Ltd.) is used for converging lens 704 and a power meter (TQ8210, available from Advantest Co.) is used for photo-sensor 705, which are then rigidly secured to an arm 706. A biaxial compact automatic rotary stage (SKIDS-60YAW (θz)–Aθ (Ver. 2.0), tradename, available from Sigma Koki Co., Ltd.) is used for goniometer 707. The angular spectrum of reflected light can be observed by arranging a target substance detecting element 107 at the center of the goniometer and rotating the rotary table and the arm in synchronism. Angle-dependent spectrums of intensity of reflected light as shown in FIG. 8 can be obtained by observing the detecting element for reference (a) and the detecting element (b) that has been made to react with the target substance. Thus, it is possible to highly sensitively measure the concentration of the insulin that is bonded to fine particles.

Example 2

It is possible to prepare agent solutions containing captor fine particles and have them react with a target substance by means of a technique similar to the one described by referring to Example 1.

(Preparation of Target Substance Detecting Element)

Figure 5A:
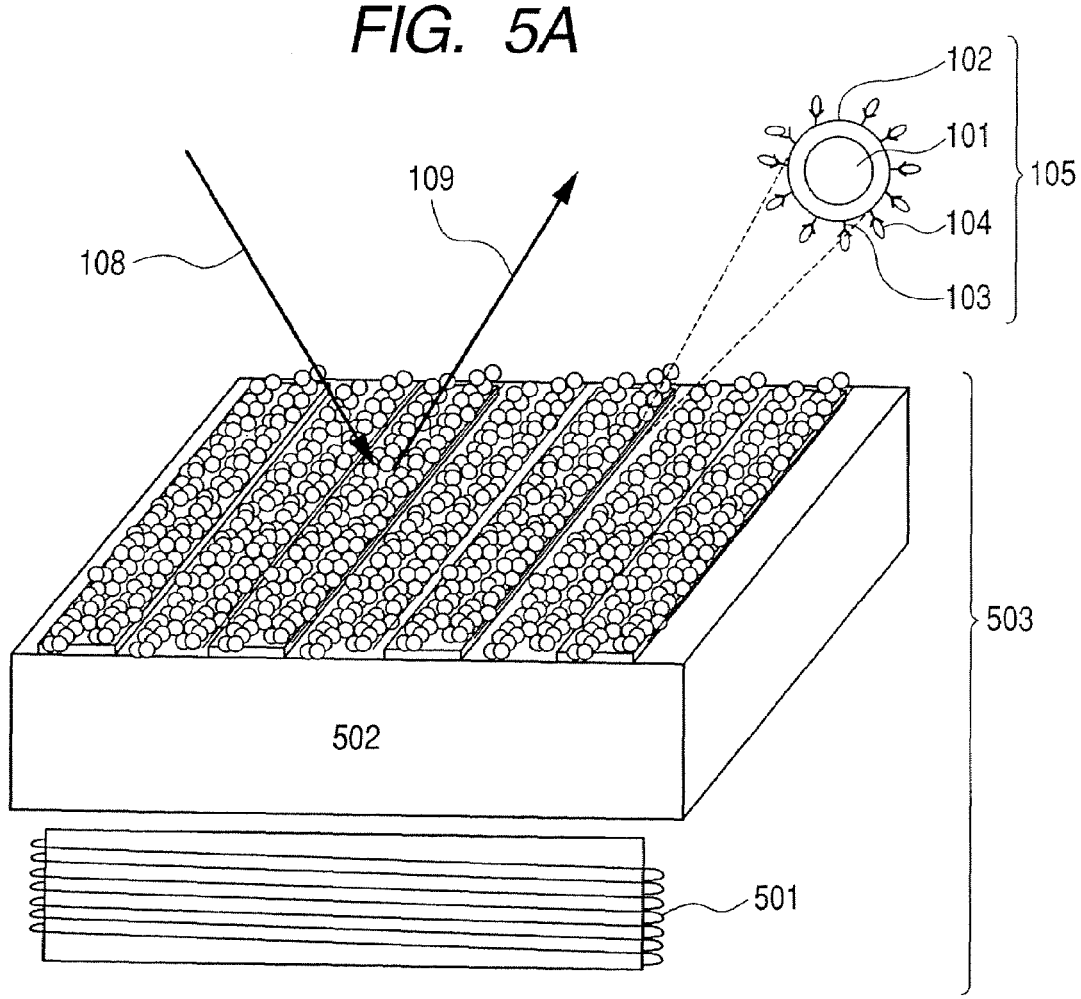
FIGS. 5A and 5B are schematic illustrations of a second embodiment of the present invention.
Figure 5B:
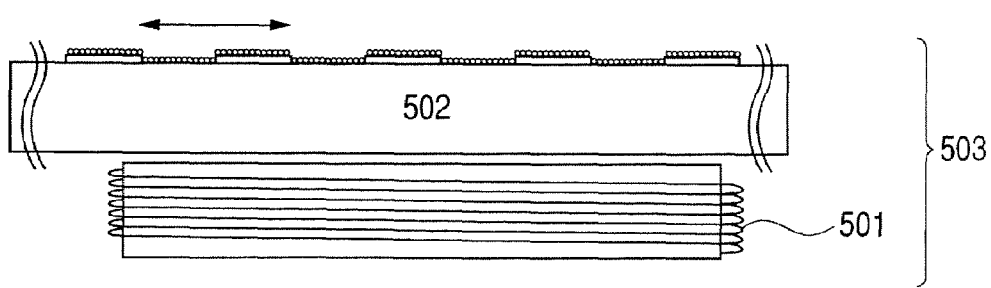

An agent solution for reference and an agent solution that has been made to react with the target substance insulin as described above are prepared and dropped onto respective base bodies so as to fix them to the respective base bodies 502 as shown in FIGS. 5A and 5B by way of a magnetic interaction in order to prepare a base member for reference and a base member for measurement that operate as diffraction gratings.

(Detection of Target Substance)

Angle-dependent spectrums of intensity of reflected light as shown in FIG. 8 can be obtained by observing the detecting element for reference (a) and the detecting element (b) that has been made to react with the target substance by means of an apparatus as shown in FIG. 7. Then, it is possible to highly sensitively measure the concentration of the insulin that is bonded to fine particles.

Example 3

It is possible to prepare agent solutions containing captor fine particles and have them react with a target substance by means of a technique similar to the one described by referring to Example 1.

(Preparation of Target Substance Detecting Element)

Figure 6:
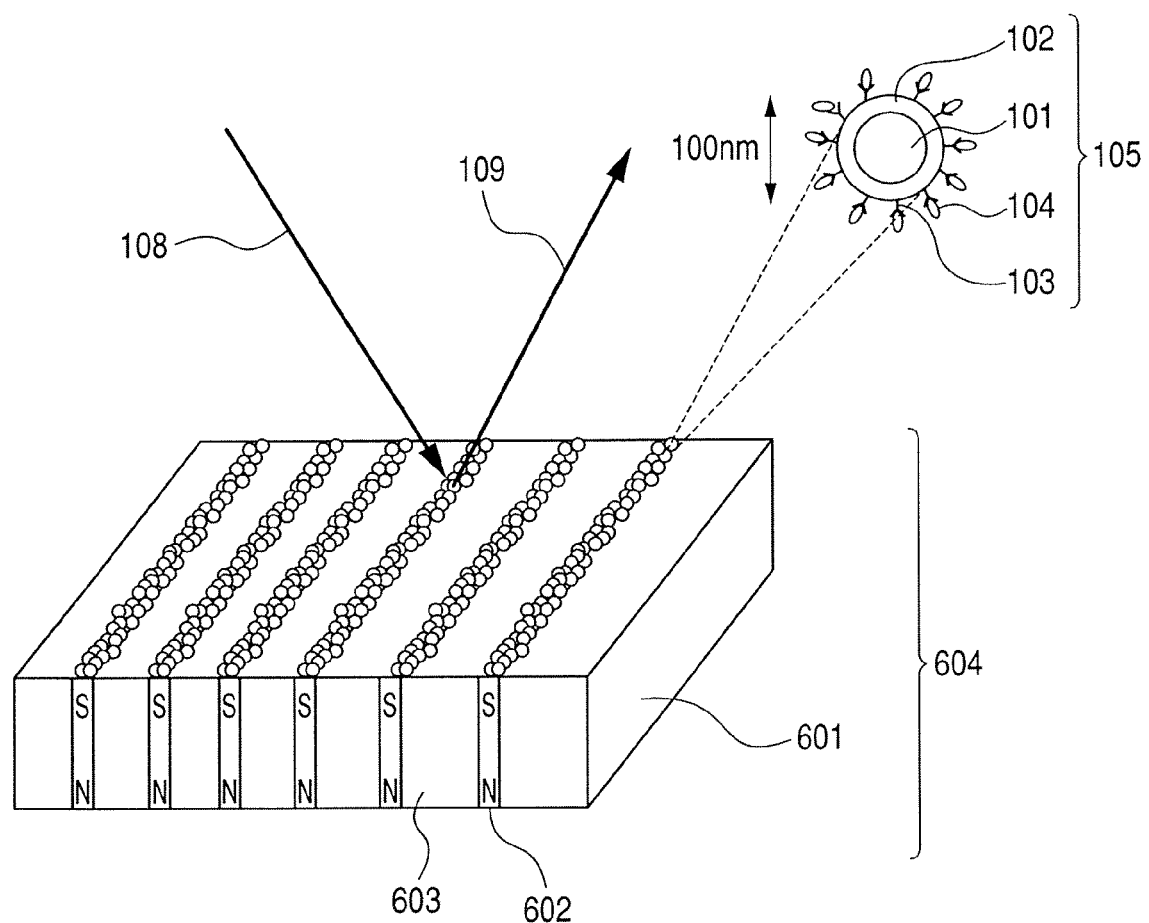
FIG. 6 is a schematic illustration of a third embodiment of the present invention.

An agent solution for reference and an agent solution that has been made to react with the target substance insulin as described above are prepared and dropped onto respective base bodies so as to fix them to the respective base bodies 601 as shown in FIG. 6 by way of a magnetic interaction in order to prepare a base member for reference and a base member for measurement that operate as diffraction gratings.

(Detection of Target Substance)

Angle-dependent spectrums of intensity of reflected light as shown in FIG. 8 can be obtained by observing the detecting element for reference (a) and the detecting element (b) that has been made to react with the target substance by means of an apparatus as shown in FIG. 7. Then, it is possible to highly sensitively measure the concentration of the insulin that is bonded to fine particles.

This application claims priority from Japanese Patent Application No. 2004-188881 filed Jun. 25, 2004, which is hereby incorporated by reference herein.

What is claimed is:

1. A detection kit for detecting a target substance in a specimen, said detection kit comprising:
   magnetic particles; and
   a base member,
   said magnetic particles each including a core of a magnetic material, a metal layer covering a surface of the core, and a target substance captor fixed onto a surface of the metal layer,
   said base member having a surface with a periodic structure operating as a diffraction grating.

2. A detection kit according to claim 1, wherein said base member includes a magnetic material.

3. A detection kit according to claim 1, wherein said periodic structure is adapted to operate as a diffraction grating relative to visible light.

4. A detection kit according to claim 1, wherein said periodic structure includes a plurality of linear protrusions and a plurality of linear depressions cyclically arranged in parallel at regular intervals.

5. A detection kit according to claim 4, wherein said linear protrusions and said linear depressions are arranged at intervals of a wavelength of visible light.

6. A detection kit according to claim 1, wherein said metal layer contains gold or silver.

7. A detection kit for detecting a target substance in a specimen, said detection kit comprising:
   magnetic particles; and
   a base member,
   said magnetic particles each including a core of a magnetic material, a metal layer covering a surface of the core, and a target substance captor fixed onto a surface of the metal layer,
   said base member having a periodic structure including a linear pattern formed by cyclically arranging a magnetic material and a non-magnetic material in parallel at regular intervals of a wavelength of visible light.

8. A detection kit according to claim 7, wherein said metal layer contains gold or silver.

9. A method for detecting a target substance in a specimen, said method comprising the steps of:
   contacting the target substance with magnetic particles, each magnetic particle including a core of a magnetic material, a metal layer covering a surface of the core, and a target substance captor fixed onto a surface of the metal layer;
   magnetically fixing the magnetic particles to a surface of a base member to form a detection element having a periodic structure operating as a diffraction grating relative to light;

irradiating the detection element with light containing a wavelength component equal to an interval of the periodic structure; and detecting light emitted from the detection element.

10. A method according to claim 9, wherein said interval of the periodic structure is within wavelengths of visible light.

* * * * *